(12) United States Patent
Melsheimer

(10) Patent No.: US 7,955,377 B2
(45) Date of Patent: Jun. 7, 2011

(54) VALVE FRAME

(75) Inventor: Jeffry S. Melsheimer, Springville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 89 days.

(21) Appl. No.: 12/357,646

(22) Filed: Jan. 22, 2009

(65) Prior Publication Data
US 2009/0187241 A1 Jul. 23, 2009

Related U.S. Application Data

(60) Provisional application No. 61/022,750, filed on Jan. 22, 2008.

(51) Int. Cl.
*A61F 2/06* (2006.01)
(52) U.S. Cl. ............... 623/1.24; 623/2.17; 623/2.18
(58) Field of Classification Search ............ 623/1.16, 623/1.24, 1.11, 2.17, 2.18
See application file for complete search history.

(56) References Cited

U.S. PATENT DOCUMENTS

| | | | |
|---|---|---|---|
| 4,643,732 A | 2/1987 | Pietsch et al. | |
| 5,358,518 A | 10/1994 | Camilli | |
| 6,200,336 B1 | 3/2001 | Pavcnik et al. | |
| 6,299,636 B1 | 10/2001 | Schmitt et al. | |
| 6,299,637 B1 | 10/2001 | Shaolian et al. | |
| 6,485,510 B1* | 11/2002 | Camrud et al. | 623/1.16 |
| 6,527,800 B1 | 3/2003 | McGuckin, Jr. et al. | |
| 6,602,286 B1 | 8/2003 | Strecker | |
| 7,201,772 B2* | 4/2007 | Schwammenthal et al. | 623/2.18 |
| 2003/0055492 A1 | 3/2003 | Shaolian et al. | |
| 2003/0130726 A1 | 7/2003 | Thorpe et al. | |
| 2003/0209835 A1 | 11/2003 | Chun et al. | |
| 2004/0186558 A1 | 9/2004 | Pavcnik et al. | |
| 2004/0225352 A1 | 11/2004 | Osborne et al. | |
| 2004/0260389 A1 | 12/2004 | Case et al. | |
| 2005/0187614 A1 | 8/2005 | Agnew | |
| 2005/0234546 A1* | 10/2005 | Nugent et al. | 623/2.11 |
| 2006/0178740 A1* | 8/2006 | Stacchino et al. | 623/2.18 |
| 2006/0265053 A1 | 11/2006 | Hunt | |
| 2007/0021826 A1 | 1/2007 | Case et al. | |
| 2007/0100435 A1 | 5/2007 | Case et al. | |

FOREIGN PATENT DOCUMENTS

WO WO2007047945 4/2007
(Continued)

OTHER PUBLICATIONS

PCT International Search Report from PCT/US2009/031537 dated Apr. 6, 2009.

(Continued)

*Primary Examiner* — David Isabella
*Assistant Examiner* — Seema Swaminathan
(74) *Attorney, Agent, or Firm* — Buchanan Nipper

(57) ABSTRACT

The disclosure relates to frames suitable for prosthetic implantable valves, and methods of treatment with such frames, to regulate blood flow and to be compliant in percutaneous delivery and, upon implantation, configured to conform to the changing shape of the body vessel or vein. The frames include at least one anchoring member attached to a support member at one or more attachments, and a valve member, preferably a monocuspid valve leaflet, attached to the support member. Preferred frames include two anchoring members with the support member in between the anchoring members. The support member preferably has a semielliptical shape and extends diagonally to sealingly contact the wall of the body vessel.

16 Claims, 6 Drawing Sheets

FOREIGN PATENT DOCUMENTS

| | | |
|---|---|---|
| WO | WO 2007/139677 | 12/2007 |
| WO | WO2009067432 | 5/2009 |

OTHER PUBLICATIONS

PCT Written Opinion from PCT/US2009/031537 dated Apr. 6, 2009.

European Patent Office, Written Opinion of the International Searching Authority, for International application No. PCT/US2008/083870.

World Intellectual Property Organization, International Application No. PCT/US2008/083870 (Int. Pub. No. WO2009/067432) and published with the International Search Report, Feb. 18, 2009, p. 1-52.

International Bureau of WIPO, Notification Concerning Transmittal of International Preliminary Report on Patentability, for International Application No. PCT/US2008/083870, Jun. 3, 2010.

* cited by examiner

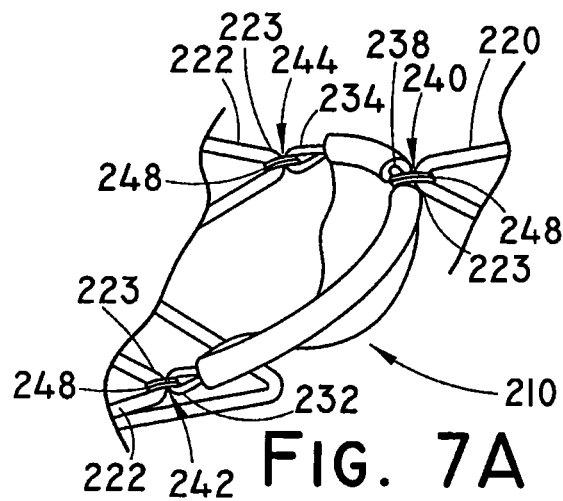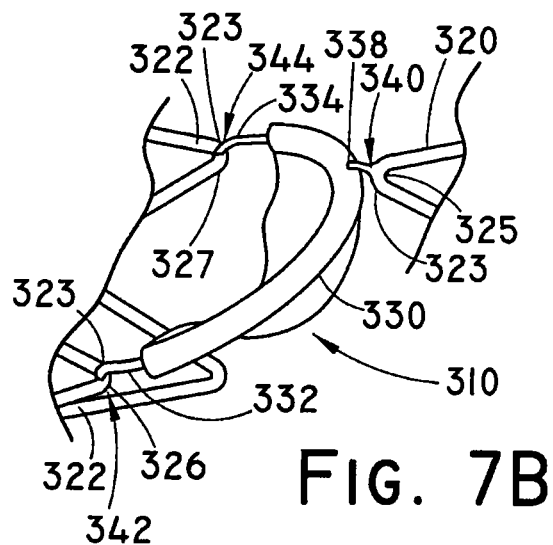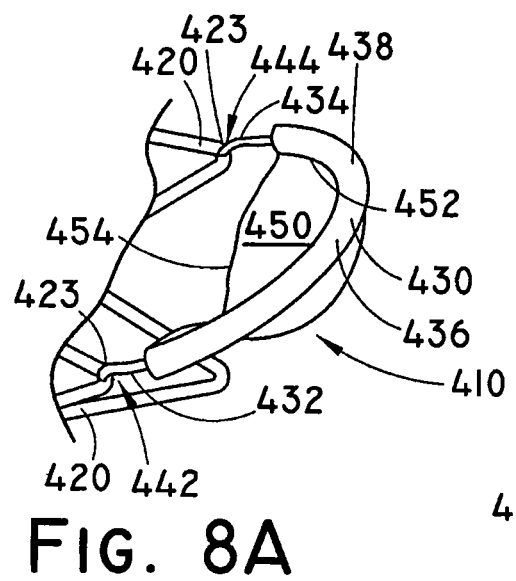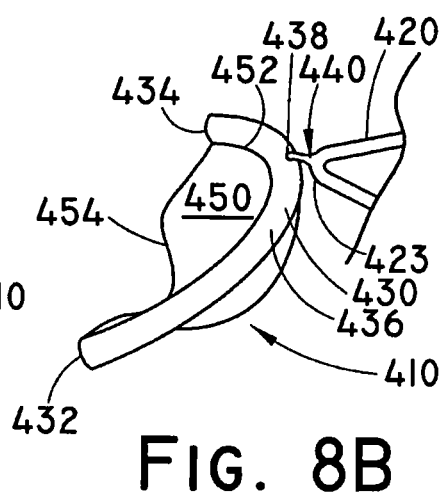

VALVE FRAME

PRIORITY CLAIM

This application claims the benefit of provisional U.S. Patent Application Ser. No. 61/022,750, filed Jan. 22, 2008, which is incorporated herein by reference in its entirety.

TECHNICAL FIELD

The present disclosure relates to implantable medical devices. More particularly, the disclosure relates to support frames for prosthetic implantable valves adapted for percutaneous implantation within a body vessel, as well as methods of treatment pertaining to the implantation of the prosthetic valves.

BACKGROUND OF THE INVENTION

Many veins of the human body or animals include natural valves that aid in the return of blood flow toward the heart. These natural valves may prevent blood from pooling in the lower legs and feet. The proper function of these venous valves is especially important during standing or sitting when the weight of blood in the vein can slow blood flow toward the heart. Problems can arise when these venous valves fail to function properly. For example, venous valves can become incompetent or damaged by disease such that the backflow of blood is not prevented. When this occurs, blood pressure builds up and the veins and their valves become dilated, particularly in the lower extremities. If enough pressure builds up, the condition of venous insufficiency may develop. The severity of this condition is substantial, resulting in swelling, extensive pain, deformities, and, in the most severe cases, the development of ulcers can occur. If these ulcers become infected, amputation may ultimately be necessary to save the patient's life.

Currently, there is no proven cure for venous insufficiency. Basic treatments include elevation of the legs or the use of compression stockings. If surgery is determined to be necessary, vein stripping is typically performed, which involves the removal of the incompetent or damaged vein(s). Other surgical methods involve valvular reconstruction or transplantation.

Recently, the development of synthetic and biological prosthetic valves has been employed in an attempt to return normal pressure to the veins. For example, U.S. Pat. No. 6,299,637 describes a synthetic venous valve for replacing incompetent native venous valves. There are a variety of these valves described in the art, which are generally designed to allow normal flow of blood back to the heart, while preventing retrograde flow. However, blood flow within a vein is intermittent and bidirectional, subject to constant fluctuation in pressure and volume. As a result, the shape of a lumen of a vein can undergo dramatic dynamic change resulting from these varying blood flow velocities, pressures and volumes therethrough. Many design considerations, consequently, regarding artificial valves for the venous system are taken into account. For example, U.S. Patent Application 2007/0038291 describes implantable frames configured to minimize the surface area of the frame in contact with the body vessel. One primary consideration includes the ability of the frame and the valve to conform to the dynamic fluctuations in the shape of the lumen of the vein. For example, U.S. Patent Application 2008/0183280 describes implantable frames configured to change shape in response to changes in a body vessel cross-section. Another primary consideration is the ability of the valve to be implanted in a body vessel having a variable diameter along the length of a site of implantation, or a branched body vessel site of implantation.

What is needed is an intraluminally-placed medical device, such as a support frame, that provides structure for an artificial valve and that is compliant to be delivered percutaneously and, upon implantation, configured to prevent migration within the body vessel and minimize irritation of the body vessel. In addition, there remains a need for a support frame configured to conform to the changing shape of the lumen of the vein. There also remains a need for a support frame configured with a radial strength to maintain patency of a body vessel while supporting a means for regulating fluid within the body vessel.

SUMMARY

In a first example, a frame suitable for prosthetic implantable valves is provided. The frame includes a first anchoring member and a second anchoring member, together defining a fluid flow path about a longitudinal axis. The second anchoring member is longitudinally spaced from the first anchoring member. The frame further includes a support member curved in the shape of a semiellipse. The support member has a first end, a second end, and a middle region between the first and second ends. The middle region includes a vertex portion. The support member is positioned between the first and second anchoring members, and a first attachment connects the vertex portion to the first anchoring member, and a second attachment connects one of the first end and the second end to the second anchoring member.

In a second example, methods for regulating fluid flow within a body vessel with one of the many valve devices are provided. The methods can include a step of loading an intraluminally-implantable valve device, as described above, in a compressed configuration into a delivery catheter. A step of inserting the delivery catheter into a body vessel and a step of translating the delivery catheter to a treatment site may also be provided. The method may also include deploying the intraluminally-implantable valve device by secureably placing the device in an expanded configuration at the treatment site. The treatment site may be a body vessel having a divergent or convergent diameter along the length of the implanted valve device. Methods for withdrawing the delivery catheter from the body vessel may also be provided.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

FIG. 7A is a perspective view of one example of a frame including an attachment with bound wire.

FIG. 7B is a perspective view of one example of a frame including an attachment integrated with support member.

FIG. 8A is a perspective view of one example of a frame in the expanded configuration.

FIG. 8B is a perspective view of one example of a frame in the expanded configuration.

DETAILED DESCRIPTION

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

DEFINITIONS

The terms "proximal" and "distal" will be used to describe the opposing axial ends of the medical device, as well as the axial ends of various component features. The term "proximal" may refer to the direction of antegrade venous blood flow toward the heart, while "distal" may refer to a direction of retrograde venous blood flow away from the heart.

The term "circumferential" or "circumferentially" refers to a direction or displacement measured along the exterior surface area of an implantable frame that is transverse to the longitudinal axis of the implantable frame.

Unless otherwise indicated, the term "longitudinal" or "longitudinally" refers to a direction measured along the longitudinal axis of the medical device, or a portion thereof such as an implantable frame. The term "longitudinally opposite" means positioned in a distal or proximal direction along the exterior surface of a medical device, such as an implantable frame, parallel to the longitudinal axis of the implantable frame.

Terms such as "preferably," "desirably," "commonly," and "typically" are not utilized herein to limit the scope of the disclosure or to imply that certain features are critical, essential, or even important to the structure or function of the disclosure. Rather, these terms are merely intended to highlight alternative or additional features that may or may not be utilized in a particular example of the present disclosure.

Frame

Figure 1A:
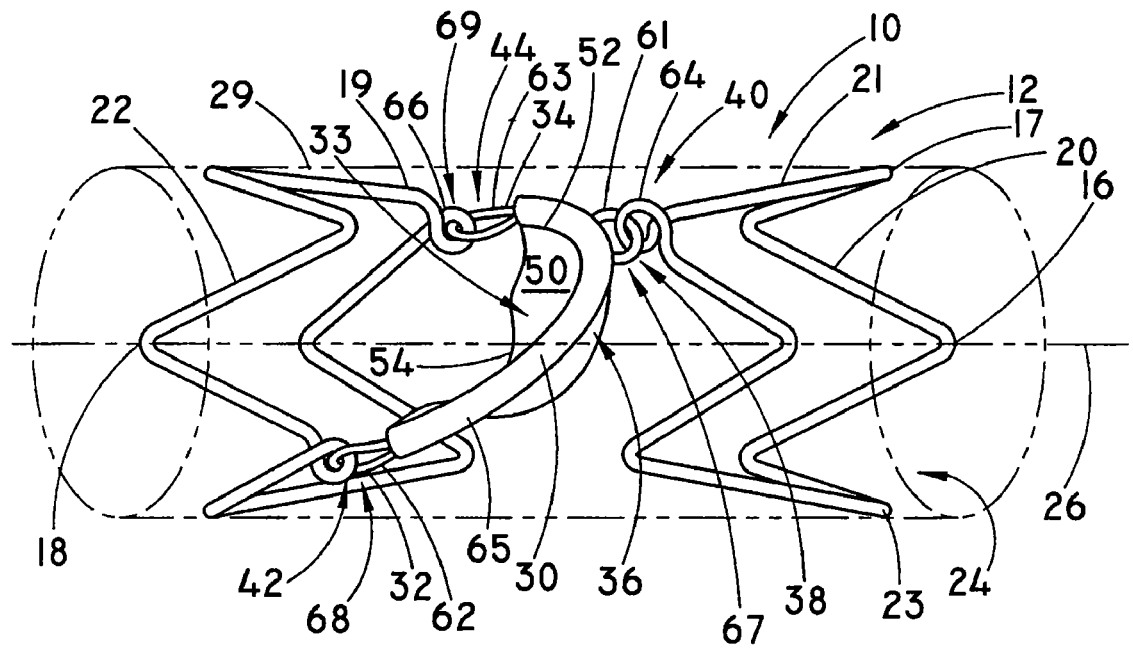
FIG. 1A is a perspective view of one example of a frame of the present disclosure in the expanded configuration.

In FIG. 1A, the frame 10 is shown in an expanded configuration 12 upon implantation within an expanding body vessel 29 having a first anchoring member 20 and second anchoring member 22. In one example, the frame 10 has a greater diameter at the first anchoring member 20 than at the position of the second anchoring member 22. Though the body vessel 29 is preferably a vein, the frame 10 can be utilized in other portions of the body as one of ordinary skill in the art would appreciate.

Referring to FIG. 1A, the frame 10 can include a support member 30 with a semielliptical shape and a valve member 50 attached to the support member 30. The frame 10 includes a proximal means for supporting the support member 30 (such as a first anchoring member 20), a distal means for supporting the support member 30 (such as a second anchoring member 22), or both. The distal means and proximal means for supporting the support member 30 can include a anchoring member, stent, stent graft, or other medical devices known by one of ordinary skill in the art. FIG. 1A illustrates a frame 10 having two anchoring members: a first anchoring member 20 and a second anchoring member 22, although the frame 10 may alternatively have one anchoring member or more than two anchoring members. The first anchoring member 20 and the second anchoring member 22 may be configured to independently radially expand to contact the wall of the body vessel 29, with the support member 30 and valve leaflet 50 disposed therebetween. In any case, the frame 10 is preferably includes a valve member 50 and is configured to treat incompetent or damaged cardiac or venous valves in mammals or to otherwise beneficially modify fluid flow in a body vessel. For example, a frame 10 having valve member 50 may be configured to replace or augment the function of natural venous valves operative in veins. The frame 10 is preferably designed to resist collapsing under the contraction of the muscle present around veins by symmetrically distributing stress and strain within the anchoring member. The frame 10 is preferably configured to provide a desired level of resistance to collapse ("hoop strength") while being sufficiently radially pliable to avoid undesirable irritation of portions of a body vessel 29 contacting each structure. Preferably, the frame 10 is structured to minimize the area of contact with the wall of a body vessel 29. The frame 10 includes at least one anchoring member 20 or anchoring member 22. For example, the frame 10 in FIG. 1A includes two anchoring members, the first anchoring member 20 and the second anchoring member 22, with the second anchoring member 22 being longitudinally spaced from the first anchoring member along a longitudinal axis 26. The first anchoring member 20 may have a proximal end 16 and a distal end 17 and the second anchoring member 22 may also have a proximal end 18 and a distal end 19.

Figure 1B:
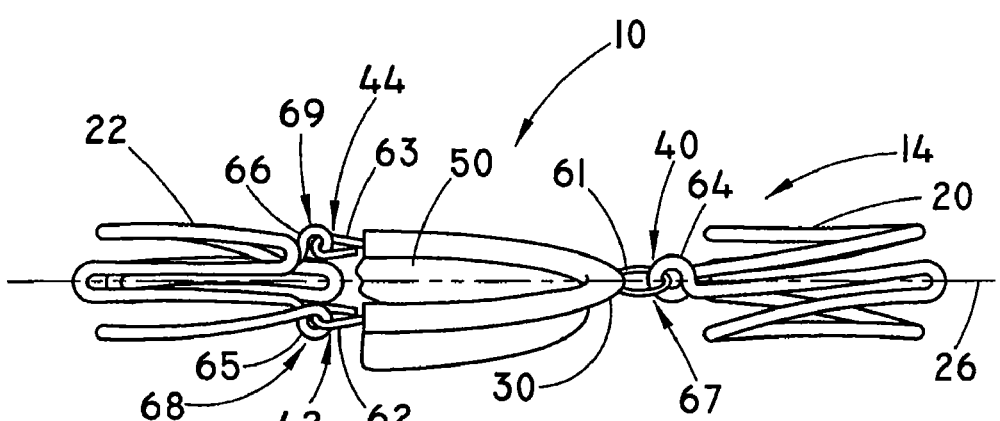
FIG. 1B is a perspective view of one example of a frame of the present disclosure in the compressed configuration.

Preferably, the frame 10 is radially moveable about a longitudinal axis 26, between an expanded configuration 12 shown in FIG. 1A and a radially compressed configuration 14. FIG. 1B shows the frame 10 in a radially compressed configuration 14 around the longitudinal axis 26. The frame 10 includes a semielliptical support member 30 positioned between a first anchoring member 20 and a second anchoring member 22. A valve member 50 is wrapped around the semielliptical support member 30 and may be gathered within the "horse-shoe"-shaped area defined within the support member 30. The semielliptical member 30 is preferably hingeably attached to the first anchoring member 20 at a first attachment 40 positioned at the vertex of the semielliptical shape of the support member 30. The opposite end of the semielliptical support member 30 may be hingeably attached to the second anchoring member 22 at both the second attachment point 42 and the third attachment point 44. Each of the first, second and third attachment points 40, 42, 44 may be formed by interconnecting loops attached to the semielliptical support member 30, the first anchoring member 40 and the second anchoring member 22, respectively, as shown in FIG. 1B. The frame 10 may be retained in the compressed configuration by any suitable means, such as a sheath portion of a catheter delivery system positioned around the outside of the frame 10. Preferably, the frame 10 is radially disposed symmetrically around a longitudinal axis 26 in the radially compressed configuration 14 when positioned within the catheter delivery system for percutaneous placement and transluminal implantation to the treatment site within the body vessel 29 and/or removal from the treatment site. The diameter of the frame 10 in the compressed configuration 14 is preferably smaller than the diameter of the frame 10 in the expanded configuration 12.

Figure 2A:
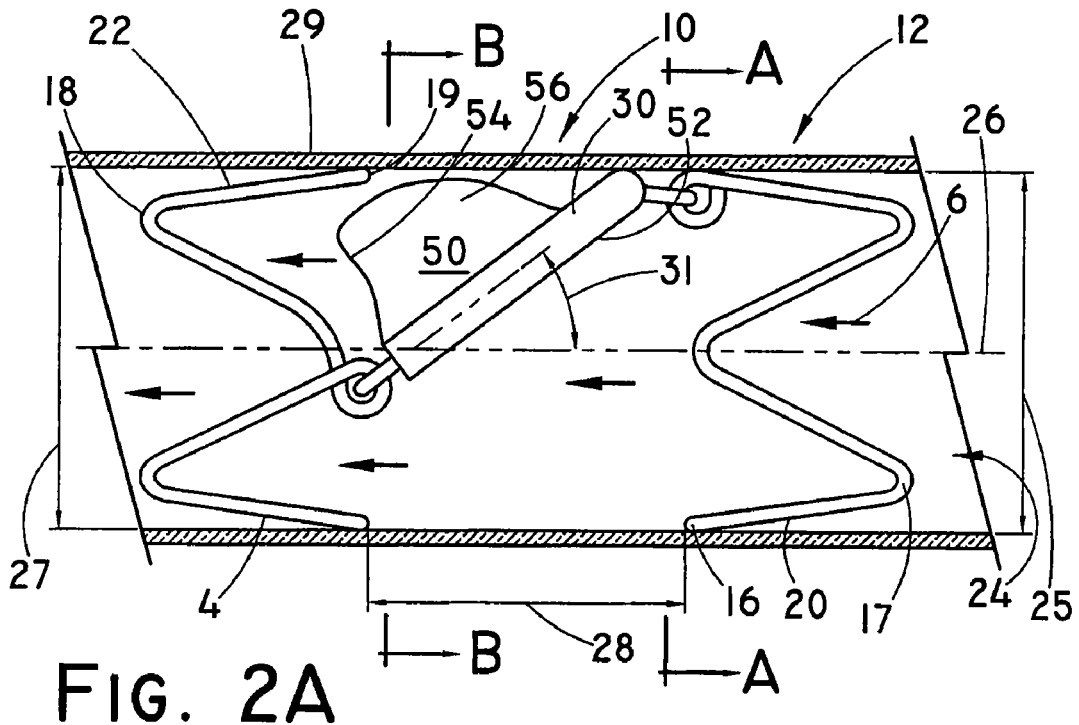
FIG. 2A is a side view of one example of a frame having a valve member in the open position.
Figure 2B:
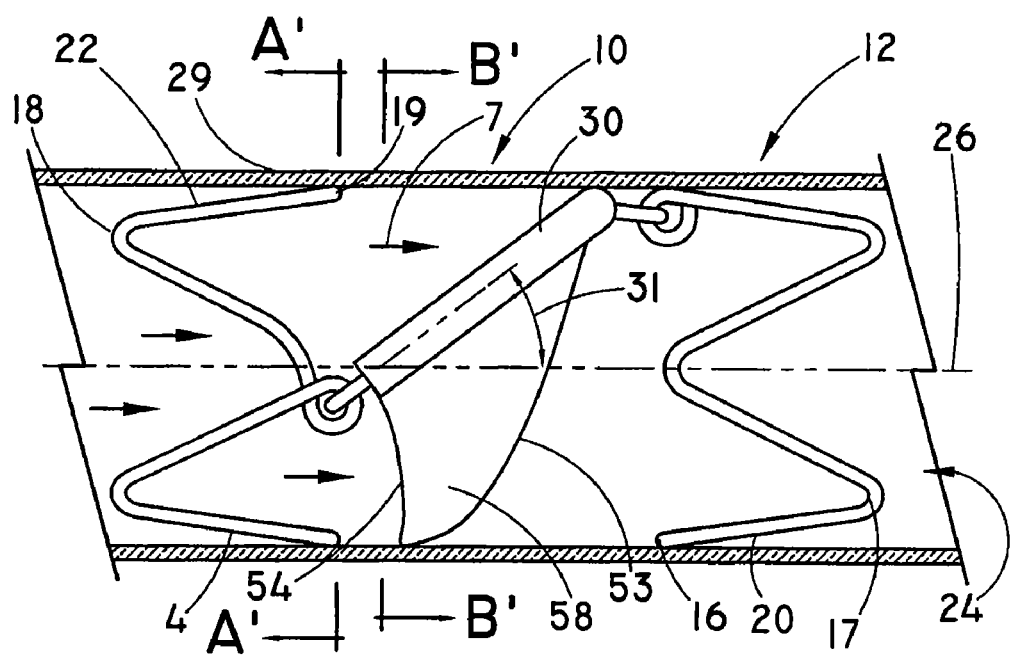
FIG. 2B is a side view of one example of a frame having a valve member in the closed position.

A side view of the frame 10 in the expanded configuration 12 is shown in FIG. 2A and FIG. 2B within the body vessel 29. Once implanted in a body vessel in the radially expanded configuration 12, the valve member 50, for example a monocuspid valve member or a leaflet, attached to the semielliptical support member 30, regulates fluid flow through the body vessel 29. The semielliptical support member 30 is oriented across at least a portion of the lumen of the body vessel 29, for example along a diagonal with a portion of the valve member intersecting the longitudinal axis 26 of the frame 10. The valve member 50 is moveable between an open configuration permitting fluid to flow in an antegrade direction 6 and a closed configuration substantially reducing or preventing fluid flow in a retrograde direction 7, opposite the antegrade direction 6.

Figure 3A:
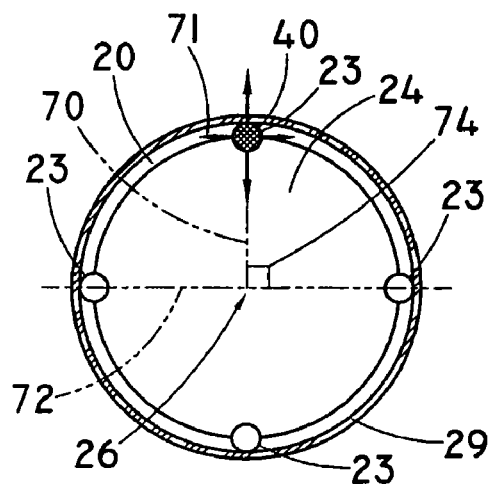
FIG. 3A is a cross sectional view taken along line A-A of the frame in FIG. 2A
Figure 3B:
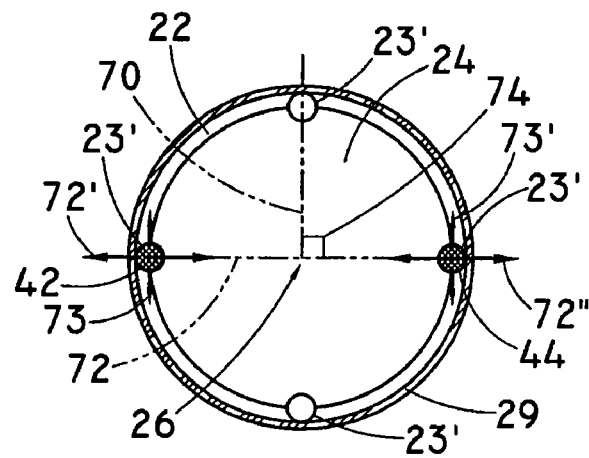
FIG. 3B is a cross sectional view taken along line A'-A' of the frame in FIG. 2B.
Figure 3C:
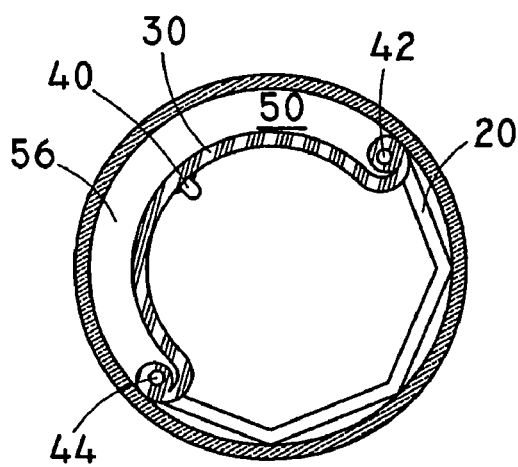
FIG. 3C is a cross sectional view taken along line B-B of the frame in FIG. 2A.
Figure 3D:
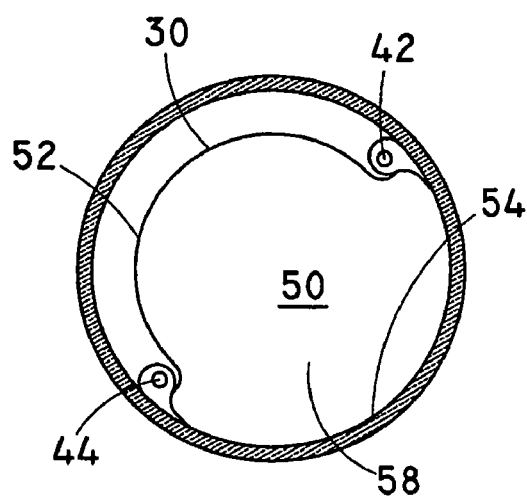
FIG. 3D is a cross sectional view taken along line B'-B' of the frame in FIG. 2B.

Preferably, the second anchoring member 22 is longitudinally spaced proximally from the first anchoring member 20 by a distance 28 as shown in FIG. 2A. FIG. 2A and FIG. 3C show the frame 10 with the valve member 50 in the open configuration; FIG. 2B and FIG. 3D show the frame 10 with the valve member 50 in the closed configuration. One example of the frame 10 is shown having a monocuspid/single-leaflet type valve as the valve member 50. One edge 52 of the valve member 50 can be affixed to the support member 30. This one edge 52 may be configured to sealingly contact the wall of the body vessel 29 when the frame 10 is implanted in the radially expanded configuration 12. The frame 10 can be oriented such that the one edge 52 of the valve member 50 may contact blood flow in an antegrade direction 6 (e.g., fluid flow through a vein toward the heart). A free edge 54 of the valve member 50 is unattached to the semielliptical support member 30 and is free to fluctuate in response to fluid flow within the body vessel between an open position 56 permitting a fluid to flow along the fluid flow path 24 and a closed position 58, or sealed position, reducing or preventing the fluid flow along the fluid flow path 24 when the frame 10 is in the expanded configuration 12 as shown in FIGS. 3C and 3D.

Frame and Support Member

Referring to FIG. 1A, the frame 10 may include a support member 30. The support member 30 can have a first end 32, a second end 34, and a middle region 36 between the first and second ends 30, 32. A vertex portion 38 can also be located in the middle region 36 of the support member 30. The support member 30 is shaped and sized to sealingly contact the wall of the body vessel 29. Preferably, the support member 30 is curved in the shape of a semiellipse. The semielliptical shaped support member 30 defines an opening 33, where a valve member 50 can be positioned. The support member 30 is designed to be rigid in a first plane and flexible in another plane to expand and compress with the frame 10. That is, the support member 30 is capable of being compressed and expanded at along the line 72 of movement as shown in FIG. 3B. However, the support member 30 is rigid in a plane connecting the vertex portion 38 and the first and second ends 32, 34.

The position of the support member 30 may be external to the anchoring member. In FIGS. 2A and 2B, the support member 30 is positioned in between the first and second anchoring members 20, 22. The support member 30 can extend across the fluid flow path 24. Preferably, the support member 30 extends diagonally at an angle 31 between about 15 degrees and about 60 degrees from the longitudinal axis 26. The support member 30 can be oriented in order for the vertex portion 38 to be exposed to oncoming blood flow 6 from the distal to the proximal direction. Preferably, the support member 30 extends distally, where the vertex portion 38 is exposed to oncoming blood flow 6.

The frame 10 preferably includes a means for supporting the semielliptical support member 30 in a desired orientation. For example, with respect to FIG. 1A, the frame 10 may include a support frame 4 moveable between the radially expanded configuration and the radially compressed configuration. In the radially expanded configuration, the frame 10 may define a hypothetical circumferential surface plane around the outer surface of the frame 10 and enclosing a tubular lumen, or fluid flow path 24, around the longitudinal axis 26. To illustrate the fluid flow path 24 in FIG. 1A, the fluid flow path 24 may extend from the proximal end 18 of the second anchoring member 22 to the distal end 17 of the first anchoring member 20. In an alternative example where the frame includes the first anchoring member 20, but not a second anchoring member 22, the fluid flow path 24 of the single anchoring member design would extend from the proximal end 16 of the first anchoring member 20 to the distal end 17 of the first anchoring member 20. Alternatively, the support frame may include the second anchoring member 22, but not the first anchoring member 20, with a fluid flow path 24 being defined within and through the second anchoring member 22.

Figure 4A:
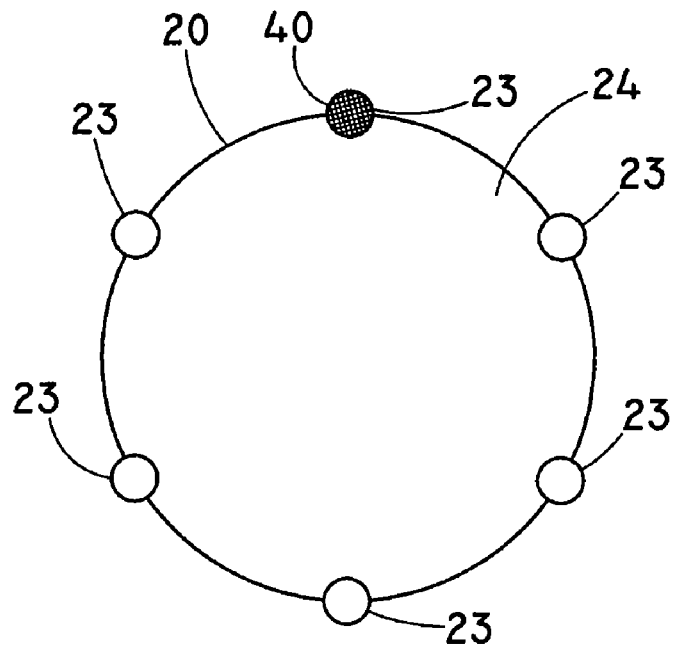
FIG. 4A is a cross sectional view of one example of the frame of the present disclosure.
Figure 4B:
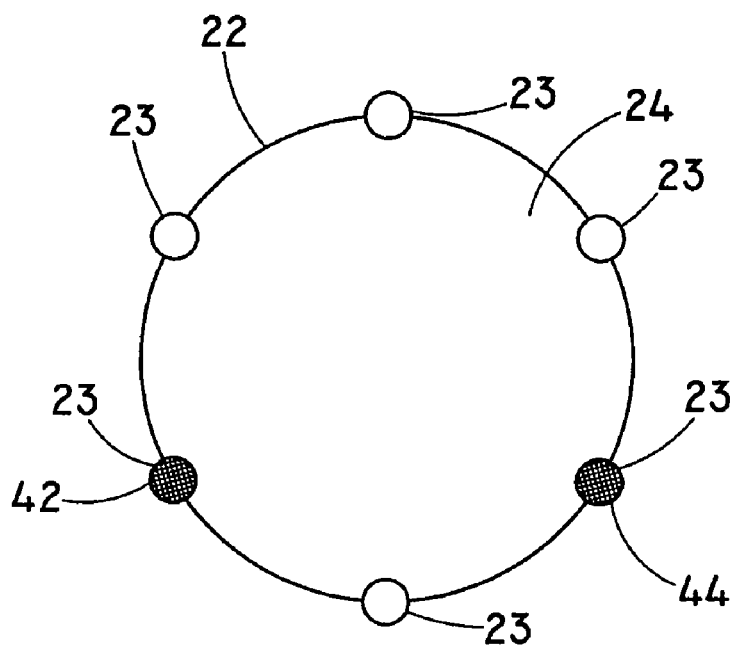
FIG. 4B is a cross sectional view of one example of the frame of the present disclosure.

Optionally, the diameter of the fluid flow path 24 may vary along a longitudinal axis 26. For example, in a multiple anchoring member design, each of the anchoring members (e.g., the first anchoring member 20 and the second anchoring member 22) may be designed to conform to the respective immediate portion of the body vessel with a non-uniform diameter. The ability of the first anchoring member 20 to expand independently from, and to a different diameter than, the second anchoring member 22 may permit the frame 10 to effectively regulate fluid flow within a body vessel having a non-uniform diameter. For example, referring to FIG. 2A and FIG. 2B, the frame 10 may be positioned proximate to an aneurysm or branched body vessel where the first anchoring member 20 may expand to a diameter the same as or different than the diameter of the second anchoring member 22. A semielliptical support member 30 hingeably attached to both the first anchoring member 20 and the second anchoring member 20 may be oriented at an angle dependent on the relative diameters of the first support member 20 and the second support member 22, so as to traverse the body vessel 29 at an angle with respect to the longitudinal axis 26 suited to regulated fluid flow therein. Referring to FIG. 2A, the first anchoring member 20 may have a first diameter 25 and the second anchoring member 22 may have a second diameter 27 in the expanded configuration 12. The first diameter 25 can be substantially similar to, greater than, or lesser than the second diameter 27. Alternatively, in a single anchoring member design, the first anchoring member 20 or the second anchoring member 22, may have the proximal end 16 and distal end 17 conform to the respective immediate portion of the body vessel with a non-uniform diameter. Additionally, one of the anchoring members 20, 22 may be positioned in a branched secondary vessel, while another of the anchoring members 20, 22 may be positioned in a connected primary body vessel. Each of anchoring members 20, 22 can be oriented in mirror symmetry to each other. That is, where each of the bends 23 of one of the anchoring members 20, 22 and the each of the bends 23 of another of the anchoring members 20, 22 mirror one another across a hypothetical plane at the center of the frame 10. In FIG. 1A, each of the first and second anchoring members 20, 22 preferably has eight struts 21 interconnected by eight bends 23. For example, the first anchoring member 20 has four bends 23 on the proximal end 16 and four bends on the distal end 17. Alternatively, each of the first and second anchoring members 20, 22 can have twelve struts 21 interconnected by twelve bends 23. Here, the first anchoring member 20 has six bends 23 on the proximal end 16 and six bends 23 on the distal end 17, as shown in FIGS. 4A and 4B that show a cross-sectional view of this arrangement.

Attachments

The support member 30 may be attached to frame 10 by at least one attachment. Preferably, the attachment is a hinge permitting the support member 30 to move relative a anchoring member to which it is attached. Most preferably, the support member is connected to one or more support rings at attachments formed by interconnecting loops or rings, permitting the support member to hingeably move along two orthogonal lines of movement (e.g., "side-to-side" and "up and down") around the attachment point. In FIG. 1A, the support member 30 includes an attachment at each end of the support member 30, and a single attachment positioned along the length of the support member 30 between these two ends. A first attachment 40 connects the vertex portion 38 of the support member 30 to the first anchoring member 20. A second attachment 42 can connect one of the first end 32 and the second end 34 to the second anchoring member 22. The first attachment 40 and the second attachment 42 can be positioned on opposite sides of the longitudinal axis 26 in the expanded configuration 12 and can be substantially aligned with the longitudinal axis 12 in the compressed configuration 14. A third attachment 44 can also connect another of the first end 32 and the second end 34 to the second anchoring member 22. Each of the attachments 40, 42, 44 is designed to permit the support member 30 to rotate at each attachment, changing the angle 31 of orientation between the support member 30 and the longitudinal axis 26 as the first anchoring member 20 radially expands or contracts relative to the second anchoring member 22. A multiple anchoring member design with three attachments may be used with a body vessel with a variable diameter or a body vessel that substantially straight. On the other hand, a multiple anchoring member design with two attachments may also be used for a body vessel that is more tortuous.

The second attachment 42 can be opposably positioned with respect to the third attachment 44 across the longitudinal axis 26. Preferably, the second attachment 42 and the third attachment 44 are opposably positioned on either side of the longitudinal axis 26, transverse to the direction of the longitudinal axis 26. FIGS. 3A and 3B are cross sectional views of the frame 10 in FIG. 2A and FIG. 2B. FIG. 3A is a cross sectional view along line A-A in FIG. 2A through the frame 10 at the proximal end 16 of the first anchoring member 20, showing the relative positions of the first attachment 40, the bends 23 of the second anchoring member 20. FIG. 3B is a cross sectional view along line A'-A' of FIG. 2B through the frame 10 at the distal end 19 of the second anchoring member 22, showing the relative positions of the second attachment 42, the third attachment 44 and the bends 23' of the second anchoring member 20. A first hypothetical cross sectional plane 70 and a second hypothetical cross sectional plane 72, each containing the longitudinal axis 26, are shown in both FIG. 3A and FIG. 3B, passing through the frame 10. The first anchoring member 20 and the second anchoring member 22 are each symmetrical about the first hypothetical cross sectional plane 70 and the second hypothetical cross sectional plane 72, which are oriented orthogonal to one another 74. The first attachment 40 is bisected by the first hypothetical plane 70 and the second and third attachments 42, 44 are each bisected by the second hypothetical plane 72. Upon moving from the radially expanded configuration to the radially compressed configuration, the first attachment 40 preferably moves along the first hypothetical plane 70, while the second and third attachments 42, 44 preferably move along the second hypothetical plane 72. In FIG. 4A the first anchoring member 20 has the fluid flow path 24 and the first attachment 40 along with six bends 23. Additionally, in FIG. 4B the second anchoring member 22 has the fluid flow path 24 and the second attachment 42 and third attachment 44, along with six bends 23.

Each of the attachments 40, 42, 44 can be formed by any structure to connect the support member 30 to the support frame 4. Optionally, one or more of the attachments 40, 42, 44 may be rigid or compliant and may be integral with the construction of the support member 30, the frame 10, or both. Each of the attachments 40, 42, 44 may also be detachable. Alternatively, the attachments may be soldered, sutured, grafted, bonded or welded. Preferably, each of the attachments 40, 42, 44 provide for some degree of movement of the support member 30 relative to the attached portion of the frame 10. This relative movement, may include a limited degree of multidirectional looseness or "play" in an attachment joint. This looseness or "play" may provide low or reduced friction and some area of movement between the support member 30 and the frame 10. Also, this area of move provides compliance and conformity when the frame 10 is in the expanded configuration 12 or is transitioned to the compressed configuration 14. For example, where the first attachment 40 is formed by interconnecting loops attached to the support member 30 and the first anchoring member 20, the looseness may be provided by an inner loop having an outer diameter that is smaller than the inner diameter of the exterior loop.

Each attachment may have a freedom of movement while the frame 10 is in the expanded configuration 12 or the compressed configuration 14. For example, the frame 10 in the expanded configuration 12 in FIG. 1A can be radially moveable to the compressed configuration 14 in FIG. 1B by the movement by the first attachment 40 toward the longitudinal axis 26 along the plane 70 of movement in FIG. 3A and by the movement of the second attachment 42 and the third attachment 44 toward the longitudinal axis 26 along their respective vertical planes 72', 72" of movement in FIG. 3B. The plane 70 of movement of the first attachment 40 is perpendicular 74 to the plane 72 of movement of the second attachment 42, the third attachment 44, or both, respectively. The first attachment may also have a second plane 71 of movement that is substantially parallel to the plane 72 of movement. However, the degree of movement along the plane 71 of movement is substantially less than the degree of movement along the plane 70 of movement. Likewise, the second attachment may also have a plane 73 of movement that is substantially parallel to the plane 70 of movement of the first attachment 40. However, the degree of movement of the second attachment along this plane 73 of movement is substantially less than the planes 72'. The third attachment may also have a plane 73' of movement that is substantially parallel to the plane 70 of movement of the first attachment 40. However, the degree of movement of the third attachment along this plane 73' of movement is substantially less than the lines 72". This degree of movement and the frame design can allow the frame 10 to be manipulated within the body vessel 29 during percutaneous delivery of the frame 10. A sheath can be removed to initially expose the second anchoring member 22 and allow for the second anchoring member 22 to expand into the expanded configuration. The second anchoring member 22 will be maintain is position within the body vessel 29, while the support member 30 and the first anchoring member 20 is manipulated. With the support member 30 and the first anchoring member 20 in the sheath, the sheath and catheter can be repositioned distally or proximally before the sheath is removed to expose the support member 30 and the first anchoring member 22.

One or more of the attachments may include an interconnected loop, as shown in FIGS. 1A and 1B. Here, the first attachment 40 can connect a first loop 61 of the vertex portion 38 to a fourth loop 64 of the first anchoring member 20 to form a hinged attachment or first hinge 67. The thickness of the first loop 61 can be greater than or lesser than the thickness of the fourth loop 64. If more than one attachment is present, then the second attachment 42 can connect a second loop 62 of the first end 32 to a fifth loop 65 of the second anchoring member 22 to form another hinged attachment or a second hinge 68, and the third attachment 44 can connect a third loop 63 of the second end 34 to a sixth loop 66 of the second anchoring member 22 to form another hinged attachment or a third hinge 69. The thickness of the second loop 62 can be greater than or lesser than the thickness of the fifth loop 65. The thickness of the third loop 63 can be greater than or lesser than the thickness of the sixth loop 66.

Figure 5:
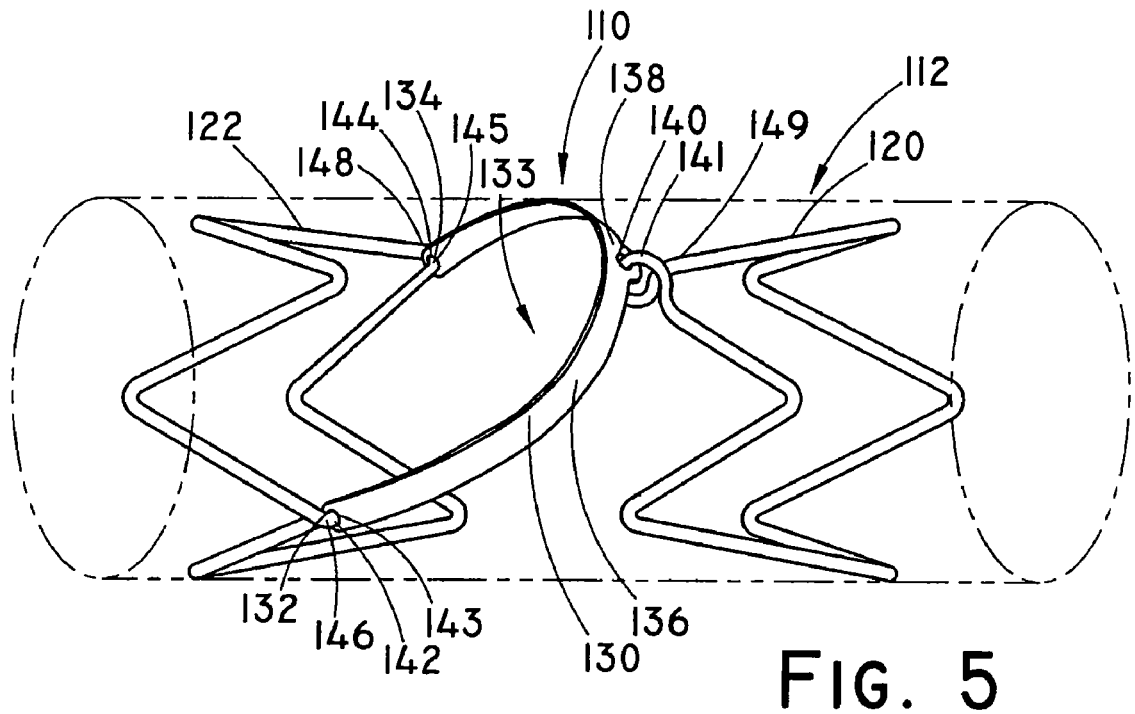
FIG. 5 is a perspective view of one example of a frame in the expanded configuration.

FIG. 5 illustrates another example of a frame 110 having an opening 133 (before attachment of the valve leaflet to the support member 130) in an expanded configuration 112. Instead of interconnected loops, the attachments include an aperture through the support member 130 where the support frame 104 connects. Here, the first attachment 140 can connect a first aperture 141 of the vertex portion 138 of the middle region 136 to an interconnected loop 149 of the first anchoring member 120. If more than one attachment is present, then the second attachment 142 can connect a second aperture 143 of the first end 132 to a first bar member 146 of the second anchoring member 122. The third attachment 144 can connect a third aperture 145 of the second end 134 to a second bar member 148 of the second anchoring member 122.

FIG. 7A illustrates an example of a frame 210 having attachments including bound wire 248. Here, the first attachment 240 can include a wire 248, looping and tying the vertex portion 238 to a bended portion 223 of the first anchoring member 220. If more than one attachment is present, then the second attachment 242 can include a wire 248, looping and tying the first end 232 to a portion of the second anchoring member 222. The third attachment 244 can similarly include a wire 248, looping and tying the second end 234 to a portion of the second anchoring member 222.

An example having the attachment integrated with the support member and more than one anchoring member is illustrated in FIG. 7B. The term "integrated" or "integrating" refers to each of the attachments 40, 42, 44 and the support member 30 being a uniform structure, or refers to each of the attachments 40, 42, 44 and the frame 10 being a uniform structure. Alternatively, the attachment, the support member, and the anchoring member being a uniform structure. In FIG. 7B, the first attachment 340 includes integrating the vertex portion 338 of the support member 330 to a portion 325 of the first anchoring member 320. If more than one attachment is present, then the second attachment 342 includes integrating the first end 332 to a portion 326 of the second anchoring member 322. The third attachment 344 can likewise integrate the second end 334 to a portion 327 of the second anchoring member 322. In these examples, integrated connections may be by welding or other suitable connecting means. Other integrated connection means include the use of a binder, heat, or chemical bond, and/or attachment by mechanical means, such as pressing, welding or suturing.

Valve Member and Monocuspid Valve Leaflet

Frames 10 may be used to regulate fluid flow by attaching a means for regulating fluid flow 6, such as a valve member 50, to any support member 30 described according to any of the examples. One or more frames including one or more valve members can be implanted within a tubular body vessel 29 of a patient, especially a human, including for example in veins or arteries, to regulate fluid flow therein. Preferably, the valve member 50 is a single leaflet type valve or monocuspid valve member. A non-limiting example of a suitable frame 10 including a valve member 50 is shown in FIG. 1A, which includes a flexible monocuspid valve member as the valve member 50 attached to a support member 30 described herein.

Referring back to FIGS. 1A-2B, the frame 10 can include the valve member 50. The valve member 50 can be attached to the support member 30 and positioned with the opening 33 of the support member 30. Preferably, the valve member 50 has a first edge 52 and a second edge 54. The first edge 52 can be disposed or attached on the middle region 36 of the support member 30, while the second edge 54 can extend between the first end 32 and the second end 34 of the support member 30 and can be movable across the fluid flow path 24. Since the second edge 54 can be moveable, the second edge 54 can have an open position 56, as shown in FIGS. 2A and 3C. The second edge 54 can have and a closed, or substantially closed, position 58 to regulate fluid flow 6 through fluid flow path 24 of the anchoring member, as shown in FIGS. 2B and 3D.

In a vein, blood flow occurs in a pulsatile fashion, with surges in antegrade fluid flow 6 occurring between intermittent retrograde fluid flow 7. A frame 10 preferably provides a one-way valve member that permits intermittent antegrade blood flow 6 while minimizing the retrograde fluid flow 7 in the opposite direction. The valve member 50 is a flexible structure configured to moveably traverse the fluid flow path 24 of the frame 10, and, where the valve member is a monocuspid valve member, configured to sealably engage the opposite wall of the body vessel 29. The valve member 50 may be configured as a flexible material attached to the support member 30 and positioned within the opening 33 of the support member 30.

The valve member 50 may be securably mounted to the support member 30 by any suitable means. The valve member 50 material can be attached to the support member by any appropriate attachment means, including but not limited to, adhesive, fasteners, and tissue welding using heat and/or pressure. Alternatively, the valve member 50 may be formed on the support member by any appropriate means, including but not limited to vapor deposition, spraying, electrostatic deposition, ultrasonic deposition, or dipping. One or more valve member 50 can be attached to the support member by other methods. In one example, a sheet of material is cut to form a valve member 50 and the first edge 52 of the member 50 are wrapped around portions of a support member and portions of the valve member 50 sealably connected together to fasten the valve member 50 around the support member. For example, one edge of a sheet of valve member 50 material can be wrapped around a portion of the support member and held against the body of the valve member 50, so that the valve member 50 material forms a lumen enclosing a portion of the frame 10. A small amount of a suitable solvent is then applied to the first edge 52 of the valve member 50 material to dissolve the first edge 52 into an adjacent portion of the valve member 50 material and thereby seal the material around the support member 30. The valve member 50 may be attached to the support member 30 by many different methods, including attachment resulting from radial pressure of the support member 30 against the valve member 50, attachment by means of a binder, heat, or chemical bond, and/or attachment by mechanical means, such as welding, suturing, sewing, threading, bonding, clamping, or otherwise affixed onto the support member.

Figure 6:
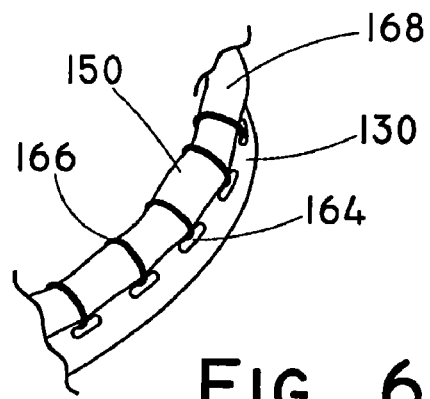
FIG. 6 is a perspective view of one example of a frame including a valve member attached to a support member.

The valve member 50 material may be shaped to form the valve member 50 that is attached to a portion of a support member 30 using stitching through the valve member 50 material and around a portion of the support member 30, adhesives, tissue welding or cross linking to directly join the valve member 50 material to the support member 30. A valve member 50 attached to a support member 30 can be permitted to move relative to the support member 30, or the valve member 50 can be substantially fixed in its position or orientation with respect to the support member 30 by using attachment configurations that resist relative movement of the valve member 50 and the support member 30. Yet, in another example illustrated in FIG. 6, the valve member 150 is attached around a tubular support 168. The valve member 150 and the tubular support 168 are attached to the support member 130, which has a plurality of eyelets 164 by means of stitching, suturing, or wire 166 binding. The wire 166 wraps circumferentially around the valve member 150 and the tubular support 168 and through the eyelets 164 of the support member 130.

The valve member 50 can be formed from a suitably flexible material to in response to fluid flow contacting the surface, and can be sized to extend transversely across the fluid flow path 24 of at least one anchoring member, in a path substantially perpendicular to the longitudinal axis 26. The valve member 50 can be oriented with the open end of the cone shape facing the direction of longitudinal retrograde fluid flow 7 through fluid flow path 24. Referring to FIGS. 2A and 2B, during retrograde fluid flow 7, blood passes the second edge 54 along the first end 51 of the valve member 50, urging the second edge 54 to transversely cross the fluid flow path 24 and sealably engage the wall of the body vessel 29 as blood fills the interior (i.e. "cup") portion of valve member 50. The valve leaflet 50 quickly fills with the retrograde flowing blood, preventing retrograde fluid flow 7 from flowing through the frame 10 and causing the valve member 50 to assume the closed position 58 shown in FIGS. 2B and 3D. In the closed position 58, blood fills the interior cone or pocket of the valve member 50, which completely fills the fluid flow path 24 and prevents retrograde fluid flow 7 through the frame.

Referring to FIGS. 2A and 2B, when blood flow 6 in the antegrade direction occurs, antegrade fluid flow 6, blood exerts pressure on the second end 53 of the valve member 50, urging the second edge 54 back across the fluid flow path 24 and forcing out fluid collected in the interior cone or pocket portion of the valve member 50. As the valve member 50 opens, the second edge 54 is forced out toward body vessel 29 wall to assume the open position 56 shown in FIGS. 2A and 3C, opening the valve member 50 and allowing antegrade fluid flow 6, or blood to flow in an antegrade direction through the frame 10.

Alternatively, the valve member 50 incorporating a multi-cuspid leaflet configuration may be utilized in the frame 10. In this example, the frame 10 can have multiple leaflets configured in such a manner to allow the leaflets to co-apt within the fluid flow path 24 of the frame 10. The valve member 50 can have any suitable shape. Preferably, the valve member 50 includes one or more edges attached to a support member 30 and extend within the lumen. The valve member 50 preferably have (n) edges and (n−1) edges of each valve member 50 preferably contact the support member 30, where (n) is an integer equal to 2 or greater. Valve leaflets with (n) of 2, 3, or 4 are preferred, although valve members 50 with other shapes can also be used. Preferably, at least 2 edges of each valve member 50 are attached to a valve support member 30, and at least one edge of each valve member 50 is a leaflet free edge that is not attached to any support member 30.

A wide variety of materials acceptable for use as a valve leaflet 50 are known in the art, and any suitable material can be utilized. The material chosen need only be able to perform as described herein, and be biocompatible, or able to be made biocompatible. Examples of suitable materials include natural materials, and synthetic materials.

In certain examples of the present disclosure, the valve member 50 is formed from a flexible material comprising a naturally derived or synthetic collagenous material, and especially an extracellular collagen matrix material. Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucosa (SIS). When implanted, SIS can undergo remodeling and can induce the growth of endogenous tissues upon implantation into a host. The support member 30 and the first edge 52 of the valve member 50 may sealingly contact the wall of the body vessel 29 by radial force until the ingrowth of cells retains the support member 30 and the first edge 52 against the wall of the body vessel 29. SIS has been used successfully in vascular grafts, urinary bladder and hernia repair, replacement and repair of tendons and ligaments, and dermal grafts. SIS is particularly well-suited for use as valve members, such as leaflets. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present disclosure, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in U.S. Pat. No. 7,087,089 (filed Jun. 28, 2002) and International Patent Application Serial Number PCT/US02/20499, filed Jun. 28, 2002, and published Jan. 9, 2003 as International Publication Number WO03002165, the contents of which are incorporated herein by reference. In one example of the disclosure, the ECM material is porcine SIS. SIS can be prepared according to the method disclosed in U.S. 2004/0180042A1, published Sep. 16, 2004, the contents of which are incorporated herein by reference. In addition to xenogenic biomaterials, such as SIS, autologous tissue can be harvested as well. Additionally elastin or elastin like Polypeptides (ELPs) and the like offer potential as a material to fabricate the flexible covering or discrete shaping members to form a device with exceptional biocompatibility. Another alternative is use of allografts such as harvested native valve tissue. Such tissue is commercially available in a cryopreserved state.

In one aspect, the valve member 50 is formed from explanted biological tissue, such as aortic tissue, that is treated in a manner that improves the biocompatibility of the tissue for an intended use. For example, the tissue may be treated to improve resistance to post-implantation mineralization. One preferred method is described in U.S. Pat. No. 5,595,571 (filed Apr. 18, 1994), incorporated by reference herein in its entirety, which involves exposing biological material including cellular and non-cellular structural components to a buffered solution having a pH in the range from about 5.0 to about 8.0 and a temperature in the range from about 12° C. to about 30° C. for a sufficient amount of time to facilitate the degradation of cells by autolytic enzymes within the cells, whereby at least one region of the biological material is rendered substantially acellular while preserving the overall structural integrity and non-cellular structural components of the biological material The exposure occurs prior to any fixation of the biological material. Other suitable tissue treatments are described in the following references, all of which are incorporated herein by reference in their entirety: U.S. Pat. Nos. 5,720,777, 5,843,180 and 5,843,181 (Biological Material Pre-fixation Treatment); U.S. Pat. No. 4,798,611 (Enhancement of Xenogenic Tissue by treatment with glutaraldehyde and then irradiation); U.S. Pat. No. 4,813,958 (Cross-linked anisotropic mammalian diaphragm in surgical reconstruction); U.S. Pat. No. 3,966,401 (Tissue for Implantation so as to Provide Improved Flexibility by Tissue subjecting tissue to tanning fluid when under pressure until the tissue assumes a natural configuration during tanning in Tanning fluids including 4% formaldehyde and 2% glutaraldehyde); U.S. Pat. No. 4,800,603 (Tissue Fixation with Vapor by subjecting tissue to a vapor of a fixative while the tissue is unstressed); and U.S. Pat. Nos. 4,813,964 and 4,813,958 (Cross-linked anisotropic xenogenic diaphragm tissue in flexor tendon pulley reconstruction, such as a method of tissue replacement for nonfunctional flexor tendon pulleys including replacing the flexor tendon pulleys with anisotropic, cross-linked mammalian, bovine or porcine diaphragm which is characterized in that the diaphragm has one smooth side and one fibrous side, the smooth side being placed against the flexor tendon). Preferably, the explanted tissue explanted tissue is pre-treated by performing at least one of the following steps: maintaining the explanted tissue at a pH in the range from about 5.0 to about 8.0 and a temperature in the range from about 12° C. to about 30° C. for a sufficient amount of time sufficient to effect the degradation of at least a portion of the cells by autolytic enzymes within the cells; contacting the explanted tissue with a chemical cross-linking agent and then irradiating with X-ray or gamma radiation; contacting the explanted tissue with a tanning fluid including formaldehyde or glutaraldehyde; or placing tissue explanted tissue within an atmosphere of substantially unpressurized vapor of containing glutaraldehyde, and maintaining the tissue within the atmosphere of substantially unpressurized vapor in a manner sufficient to provide substantially uniform application of the fixative solution for a period of time to cause the desired fixation of said tissue.

The valve member may be formed by joining multiple sheets of biological material together. The sheets of biological material may be hydrated or dehydrated. Optionally, an adhesive, glue or other bonding agent may be used in achieving a bond between ECM layers within a valve member. Drying or dehydration methods can also be used to fuse ECM portions of the valve member. In one preferred example, the multiple layers of ECM material are compressed under dehydrating conditions. The term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions. Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

The thickness of the valve member may be selected to provide a desired flexibility for a particular application. One way to alter the thickness of a valve member, such as a sheet formed from SIS material, is to compress it under dehydrating conditions, e.g., to vacuum press it. Another way to alter the thickness of a multi-laminate valve member material formed from form SIS material is to alter the number of material layers included therein. A typical layer thickness for an as-isolated submucosa or other ECM tissue layer used in the disclosure ranges from about 50 to about 250 microns when fully hydrated, more typically from about 50 to about 200 microns when fully hydrated, although isolated layers having other thicknesses may also be obtained and used. In the case of SIS valve member, a valve member may have a thickness of about 0.1 mm thick, and is preferably attached to the support member in the hydrated condition.

The valve member may be attached to the support member by any suitable means, including use of a biological adhesive, a cross-linking agent, sutures, heat welding, crimping, and pressure welding. Preferably, the valve member is not attached to the anchoring member(s). Suitable bonding agents may include, for example, collagen gels or pastes, gelatin, or other agents including reactive monomers or polymers, for example cyanoacrylate adhesives. As well, bonding can be achieved or facilitated using chemical cross-linking agents, such as glutaraldehyde, formaldehyde, epoxides, genipin or derivatives thereof, carbodiimide compounds, polyepoxide compounds, or other similar agents. Cross-linking of ECM materials can also be catalyzed by exposing the ECM to UV radiation, by treating the collagen-based matrix with enzymes such as transglutaminase and lysyl oxidase, and by photo cross-linking. The combination of one or more of these with dehydration-induced bonding may also be used.

The valve member 50 may also be formed from a synthetic polymeric material. Examples of suitable polymeric materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a cross-linked biocompatible polymer, chemical modification with biocompatible functional groups, and immobilization of a compatibilizing agent such as heparin or other substances.

In addition, the valve member 50 material may be a biocompatible polyurethane or derivative thereof. One example of a biocompatible polyurethane is THORALON (THORATEC, Pleasanton, Calif.), as described in U.S. Pat. Application Publication No. 2002/0065552 A1 and U.S. Pat. No. 4,675,361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer. The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference. The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts, which may be removed by contacting the material with a suitable solvent to dissolve and remove the inorganic salt after pore formation. Formation of porous THORALON is described, for example, in U.S. Pat. Nos. 6,752,826 and 2003/0149471 A1, both of which are incorporated herein by reference. Non-porous THORALON can be formed by mixing the polyetherurethane urea (BPS-215) and the surface modifying additive (SMA-300) in a suitable solvent, such as dimethyacetamide (DMAC). The composition can contain from about 5 wt % to about 40 wt % polymer, and different levels of polymer within the range can be used to fine tune the viscosity needed for a given process. The composition can contain less than 5 wt % polymer for some spray application examples. The entire composition can be cast as a sheet, or coated onto an article such as a mandrel or a mold to form a valve leaflet, which can be dried to remove the solvent.

FIGS. 8A and 8B illustrate another example of the frame 410 including one anchoring member 420, i.e., a single anchoring member design. A single anchoring design with one or two attachments may be preferably used when the diameter of the vessel is uniform or not tortuous. The frame 410 can define a fluid flow path about a longitudinal axis. The frame 410 can include a support member 430. The support member 430 may be curved in the shape of a semiellipse, and may have a first end 432, a second end 434, and a middle region 436 that is between the first and second ends 432, 434 and that includes a vertex portion 438. The support member 430 may be positioned external to the anchoring member 420 and may extend diagonally across the fluid flow path. Yet, the attachment is integrated with the anchoring member and the support member, and preferably rigid and preconfigured at an effective angle across the fluid flow path. The support member 430 can be attached to the anchoring member 420 by one of: one attachment and two attachments. The one attachment 440 may connect the vertex portion 438 to the anchoring member 420 as shown in FIG. 8B. The two attachments 442, 444 may connect the first end 432 and the second end 434 to the anchoring member 420 as shown in FIG. 8A. The valve member 450 may be attached to the support member 430. The valve member 450 may have a first edge 452 and a second edge 454, the first edge 452 being attached to the support member 430. The valve member 450 being moveable to regulate fluid flow through the fluid flow path of the anchoring member 420.

The position of each of the attachments 40, 42, 44 is generally determined by the total number of attachments. If there is one attachment as illustrated in FIG. 8B, the vertex portion 438 of the support member 430 is attached to any portion of the frame 410, or any one of the bends 423 of the anchoring member 420. If there are two attachments as illustrated in FIG. 8A, the first and second ends 432, 434 of the support member 430 can be attached to any portion of the frame 410, or any two of the bends 423 of the anchoring member 420. Alternatively, referring to FIG. 7B for reference only, one of the first and second ends 332, 334 of the support member 330 can be attached any portion of the frame 310, or to any one of the bends 323 of second anchoring member 322. Additionally, the vertex portion 338 of the support member 330 can be attached to any portion of the frame 310, or any one of the bends 323 of a first anchoring member 320. Preferably, there are three attachments as illustrated in FIG. 7B. Here, the first and second ends 332, 334 of the support member 330 can be attached to any portion of the frame 310, or any two of the bends 323 of the second anchoring member 322, and the vertex portion 338 of the support member 330 can be attached to any portion of the frame 310, or to any one of the bends 323 of the first anchoring member.

Materials and Methods of Making Support Frame and Support Member

The frame 10 may be fabricated using any suitable method known in the art. Preferably, the complete frame 10 structure is cut from a solid tube or sheet of material, and thus the frame 10 would be considered a monolithic unit. Laser cutting, water-jet cutting and photochemical etching are all methods that can be employed to form the structural frame 10 from sheet and tube stock. Still other methods for fabricating the complete frame 10 structure as previously disclosed would be understood by one of skill in the art. For example, the frame 10 may be formed by multiple anchoring members 20, 22 each having any suitable configuration, including a plurality of struts and bends forming an array of longitudinally connected hoops, or the frame 10 may comprise braided or helically wound strands. Anchoring member frames may be formed by cutting from solid tubes, weaving or folding frame members, strands or sheets of material. The frame 10 can have any suitable size. The exact configuration and size chosen will depend on several factors, including the desired delivery technique, the nature of the body vessel in which the medical device will be implanted, and the size of the vessel. The support frame can be sized so that the second, expanded configuration is slightly larger in diameter that the inner diameter of the vessel in which the medical device will be implanted.

For example, in FIG. 1A, the first anchoring member 20 or the second anchoring member 22 may be configured in various shapes, having any suitable annular array or plurality of struts 21 interconnected by a plurality of bends 23, such as a serpentine or zigzag configuration. In these examples, connections between the struts 21 and bends 23 may be preserved during laser cutting of a tube or formed by attaching frame portions by welding or other suitable connecting means. Other connection means include the use of a binder, heat, or chemical bond, and/or attachment by mechanical means, such as pressing, welding or suturing. In addition, portions of the frame 10 may be attached by applying a bonding coating. The number of the struts 21, the thickness of the struts 21, the material and composition of the struts 21 and length of the struts 21 may be selected to provide the valve device 10 with desirable properties. For example, the desired properties can be an improved contact between a portion of a valve member 50 and the wall of a body vessel 29 and/or improved symmetrical distribution of stress-strain forces within the frame 10. Adjacent struts may be connected at opposite ends in a substantially S- or Z-shaped pattern so as to form a plurality of cells. Other shaped patterns may also be used.

Alternatively, the frame 10 can also be formed from wire using wire forming techniques, such as coiling, braiding, or knitting. By welding the wire at specific locations a closed-cell structure may be created. This allows for continuous production, i.e. the components of the frame 10 may be cut to length from a long wire mesh tube. In addition, the frame 10 is constructed from sheet, wire (round or flat) or tubing. The method of fabrication can be selected by one skilled in the art depending on the raw material used. Techniques for forming frames 10 are discussed, for example, in Dougal et al., "Stent Design: Implications for Restenosis," Rev. Cardiovasc Med. 3 (suppl. 5), S16-S22 (2002), which is incorporated herein by reference in its entirety.

The support member 30 may also be fabricated using any suitable method known in the art. Preferably, the support member 30 is cut from a solid tube having a circular cross section or sheet of material having a rectangular cross section, and thus the support member 30 would be considered a monolithic unit. Laser cutting, water-jet cutting and photochemical etching are all methods that can be employed to form the support member from sheet and tube stock. In other examples, the support member 30 may be fabricated from multiple pieces of solid tube or sheet of material. Here, the pieces may be by welding or other suitable connecting means. Other connection means include the use of a binder, heat, or chemical bond, and/or attachment by mechanical means, such as pressing, welding or suturing.

When forming the frame 10 from shape memory metal such as a nickel-titanium alloy sold as nitinol, the frame 10 can be laser cut from a nitinol tube. Thereafter, the frame 10 can be subjected to a shape-setting process in which the cut tube or sheet is expanded on a mandrel and then heated. Multiple expansion and heating cycles can be used to shape-set the frame 10 to the final expanded diameter. Preferably, the final expanded diameter is equal to the desired deployed diameter of the frame 10. During expansion, the frame 10 is preferably axially restrained such that the length of the support frame 4 does not change during expansion. The finished frame 10 preferably has an austenite finish temperature less than body temperature. Thus, at body temperature, the frame 10 will self-expand to the desired deployed diameter due to the shape memory characteristic of the metal forming frame 10.

The frame 10 can be formed from any biocompatible material, such as a shape memory metal or stainless steel, or from any suitable material. Preferred materials for the frame 10, including the support member 30, include those materials that can provide the desired functional characteristics with respect to mechanical load bearing, biological compatibility, modulus of elasticity, radio-opacity, or other desired properties. For some examples, the materials used to form the frame 10 can comprise a material that exhibits excellent corrosion resistance. In some examples, the frame 10 can comprise a metal, a metal alloy, a polymer, or any suitable combination thereof, for example as a frame with multiple layers.

Preferably, the frame 10 is self-expanding comprising a material capable of significant recoverable strain to assume a low profile for delivery to a desired location within a lumen of a body vessel 29. The self-expanding material can be any of shape-memory material, a spring-like material, or an elastomeric material. After release of the compressed self-expanding frame 10 and support member 30, it is preferred that frame 10 and support member 30 be capable of radially expanding back to its original diameter or curvature or close to its original diameter or curvature. Accordingly, some examples provide frame 10 and support member 30 made from material with a low yield stress (to make the frame 10 deformable at manageable balloon pressures), high elastic modulus (for minimal recoil), and is work hardened through expansion for high strength. Particularly preferred materials for self-expanding frame 10 are shape memory alloys that exhibit superelastic behavior, i.e., are capable of significant distortion without plastic deformation. Frame 10 and support member 30 manufactured of such materials may be significantly compressed without permanent plastic deformation, i.e., they are compressed such that the maximum strain level in frame 10 and support member 30 is below the recoverable strain limit of the material.

Discussions relating to nickel titanium alloys and other alloys that exhibit behaviors suitable for frame 10 and support member 30 can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable support frames 4 can be obtained from, e.g., Memory Corp., Brookfield, Conn. One suitable material possessing desirable characteristics for self-expansion is Nitinol, a Nickel-Titanium alloy that can recover elastic deformations of up to 8% percent. This unusually large elastic range is commonly known as super-elasticity.

In one example, the frame may be coated with an abrasion resistance material. For example, a surface coating that improves abrasion resistance may be appropriate since the support rings at the attachments permit the support member to hingeably move along two orthogonal lines of movement. Hard, wear resistant, coatings can be produced on metal surfaces by heat treating the components in a carburizing and or nitriding atmosphere. Examples of this approach include a carburized layer, nitrided layer or a combined carburized and nitrided layer such as is done in ferritic carbonitriding. Metallurgical coatings can also be applied through chemical or vapor deposition. A common example of a hard coating applied through this approach is titanium nitride which is commonly used to improve the abrasion resistance of tooling and tool inserts. Other examples of chemical or vapor deposition include coating the metal surfaces with an oxide ceramic, such as alumina or zirconia; non-oxide ceramic, such as silicon nitride or silicon carbide; or other ceramic materials that are biologically inert, and yet are sufficiently hard and abrasion resistant. Pyrolytic or DLC (ie diamond like coated) carbon can also be applied through the chemical or plasma vapor deposition process in order to manufacture a coating to improve abrasion resistance. A third approach is to oxidize the metallic surface through an anodization process. Anodization is commonly used to create a TiO2 oxide coating on commercially pure titanium, titanium based alloys and shape memory alloys such as nitinol. This approach will also work for other light metals such as aluminum. In certain cases, depending upon the magnitude of the normal and subsequent frictional forces, it may be desirable to decrease the friction by using a lubricating polymer. Examples of these coatings include polyethylene, including ultra high weight molecular weight polyethylene (UHMW PE); polyetheretherketone (PEEK); polyetherketoneketone (PEKK); polycarbonate urethane (PCU); and fluorinated polymers such as polytetrafluoroethylene (PTFE). It may be appropriate in certain cases to couple an anodization treatment with a polymer to create a composite coating.

Alternatively, the frame 10 may be designed to be expanded by an outside influence, or mechanical expansion, such as by a balloon or some other device (i.e., the frames 10 are not self-expanding), temperature fluctuation, or kinematic articulation. The frame 10 and support member 30 may be manufactured from an inert, biocompatible material with high corrosion resistance, or polymer, that can be plastically deformed at low-moderate stress levels. The frame 10 can be deployed by both assisted (mechanical) expansion, i.e. balloon expansion, and self-expansion means. In examples where the frame 10 is deployed by mechanical (balloon) expansion, the frame 10 is made from materials that can be plastically deformed through the expansion of a mechanical assist device, such as by the inflation of a catheter based balloon. When the balloon is deflated, the frame 10 can remain substantially in the expanded shape. Other acceptable materials include stainless steel, titanium ASTM F63-83 Grade 1, niobium or high carat gold K 19-22. One widely used material for balloon expandable structural support frame 4 and support member 30 is stainless steel, particularly 316L stainless steel. This material is particularly corrosion resistant with a low carbon content and additions of molybdenum and niobium. Fully annealed, stainless steel is easily deformable. Alternative materials for mechanically expandable structural support frame 4 and support member 30 that maintain similar characteristics to stainless steel include tantalum, platinum alloys, niobium alloys, and cobalt alloys.

Optionally, the frame 10 and support member 30 may be formed from or coated with other materials, such as polymers and bioabsorbable polymers. The frame 10 and support member 30 or portions thereof can optionally comprise material that permits identification of the position or orientation of frame 10 and support member 30 within a body vessel 29. For some examples, the material can be selected to be sufficiently radiopaque and create minimal artifacts during magnetic resonance imaging techniques (MRI). Radiopaque markers are advantageously positioned at one or more ends of the frame 10 to aid the physician in positioning the frame 10 at a site inside a body vessel 29. For example, portions of the frame 10 can include a radiopaque material that can be identified by X-rays. For example, U.S. Pat. No. 6,409,752, issued Jun. 25, 2002 to Boatman et al., incorporated herein by reference, discloses various radiopaque materials that can be used in or on the frame 10. Alternatively, the material can be selected to be sufficiently radiolucent, or materials that facilitate visualization of the frame 10 by virtue of fluoroscopy. In other examples, the material may have a characteristic that exhibits echogenicity to facilitate visualization of the frame 10 under ultrasonic investigation.

A frame 10 can optionally be sterilized using any suitable technique known in the art, or equivalents thereto. For example, an implantable frame 10 can be sterilized using ethylene oxide sterilization, as described in AAM/ISO 11135:1994 "Medical Devices—Validation and Routine Control of Ethylene Oxide Sterilization," incorporated herein by reference in its entirety. In some examples, a sterilized implantable support frame 4 satisfies a minimum Sterility Assurance Level (SAL) of about $10^{-6}$.

Methods of Delivery and Treatment

Frames 10 can be deployed at various locations and lumens in the body, such as, for example, veins of the deep venous system, the superficial venous system, or other body vessels including vessels within coronary, vascular, nonvascular and peripheral vessels, ducts, and the like. In one example, a valve member 50 is attached to the support member 30, which is attached to the frame 10, to provide a frame that can be implanted within a vein, for instance, near an incompetent venous valve to treat venous valve insufficiency. Frames 10 of the present disclosure are desirably adapted for deployment within the vascular system, and in certain preferred examples, are adapted for deployment within the venous system. Accordingly, a frame can be adapted as a venous valve, for example, for attachment within veins of the legs or feet, to treat venous insufficiency.

The frames described herein can be configured for delivery to a body vessel 29 in a radially compressed configuration 14, and radially expanded to a radially expanded configuration 12 at a point of treatment within the body vessel 29. The overall configuration, cross-sectional area, and length of the frame 10 having a tubular configuration (compressed or expanded) may depend on several factors, including the size and configuration of device, the size and configuration of the vessel 29 in which the device will be implanted, the extent of contact between the device and the walls of the vessel 29, and the amount of retrograde flow 6 through the vessel 29 that is desired.

Preferably, the frames 10 described above can be intraluminally delivered inside the body by a catheter that supports the frame 10 in a compacted form as it is transported to the desired site, for example within a body vessel 29. Upon reaching the site, the frame 10 can be expanded and securably placed within the body vessel 29, for example by securably engaging the walls of the body vessel 29 lumen. The expansion mechanism may involve permitting the valve device to expand radially outward, for example, by inflation of a balloon formed in the distal portion of the catheter, to inelastically deform the frame and fix it at a predetermined expanded position in contact with the lumen wall. The expansion balloon can then be deflated and the catheter removed. In another technique, the frame 10 is formed of a material that will self-expand after being compacted. During introduction into the body, the frame 10 is restrained in the compacted condition. When frame 10 has been delivered to the desired site for implantation, the restraint is removed, allowing the frame 10 to self-expand by its own internal elastic restoring force. Once the frame 10 is located at the constricted portion of the lumen, the sheath is removed to expose the frame, which is allowed to expand so it contacts the lumen wall. The catheter is subsequently removed from the body by pulling it in the proximal direction, through the larger lumen diameter created by the expanded prosthesis, which is left in the body. Alternatively, the sheath can be removed to initially expose the second anchoring member 22 and allow for the second anchoring member 22 to expand in to the expanded configuration. With the support member 30 and the first anchoring member 20 in the sheath, the sheath and catheter can be repositioned distally or proximally before the sheath is removed to expose the support member 30 and the first anchoring member 22.

Frames 10 can be delivered into a body lumen using a system which includes a catheter. An appropriately sized delivery catheter can be selected by one skilled in the art for a given application. For example, some examples can be delivered using a delivery catheter selected from one or more delivery catheter sizes from the group consisting of: 3, 4, 5, 6, 7, 8, 9, 10, 11, 12, 13, 14, 15, 16, 17, 18, 19, 20, 21, 22, 23, and 24 French (F) delivery catheters, or increments of 0.1 F therebetween. In some examples, a delivery catheter sized between 3 and 24 F, or preferably between about 6 F and 16 F can be used.

The frames 10 can be placed in any medically appropriate location for a given application. For example, in some examples, the frame 10 can serve as part of a venous valve prosthetic and be implanted in the femoral vein, including at the proximal (groin), mid (mid section) or distal (adjacent to the knee) portions of the vein. Preferably, frames 10 are placed in the superficial venous system, such as the saphenous veins in the leg, or in the deep venous system, such as the femoral and popliteal veins extending along the back of the knee to the groin.

Methods of treatment preferably include the steps of loading a frame 10 in a radially compressed configuration 14 into a delivery catheter, inserting the delivery catheter into a body vessel 29, translating the delivery catheter to a treatment site, deploying the frame 10 by placing the frame 10 in an expanded configuration 12 at the treatment site to treat the subject, and withdrawing the delivery catheter from the body vessel 29. Once the frame 10 is deployed the frame 10 is secured to prevent tilting, dislodgement or migration and to facilitate an effective seal and possible incorporation within the body vessel 29.

Having described the disclosure in detail and by reference to specific examples thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. It is therefore intended that the foregoing detailed description be regarded as illustrative rather than limiting, and that it be understood that it is the following claims, including all equivalents, that are intended to define the spirit and scope of this disclosure.

I claim:

1. A frame radially moveable about a longitudinal axis between an expanded configuration and a compressed configuration suitable for prosthetic implantable valves comprising:
   a first anchoring member and a second anchoring member together defining a fluid flow path about the longitudinal axis, the second anchoring member being longitudinally spaced from the first anchoring member;
   a support member being curved in the shape of a semiellipse, the support member having a first end, a second end, and a middle region between the first and second ends and including a vertex, where the support member is positioned between the first and second anchoring members and in the expanded configuration extends diagonally at an angle between about 15 degrees and about 60 degrees from the longitudinal axis, and a first hinged attachment connecting the vertex of the support member to the first anchoring member, and a second hinged attachment connecting one of the first end and the second end to the second anchoring member.

2. The frame of claim 1, further comprising a valve member attached to the support member, the valve member being moveable to regulate fluid flow through fluid flow path of the first and second anchoring members.

3. The frame of claim 2, where the valve member comprises a leaflet having a first edge and a second edge, the first edge being attached to the middle region of the support member, the second edge extending between the first end and the second end of the support member and being movable across the fluid flow path between a open position permitting a fluid to flow along the fluid flow path and a closed position reducing or preventing the fluid flow along the fluid flow path, when the frame is in the expanded configuration.

4. The frame of claim 1, where each of the first anchoring member and the second anchoring member has a proximal end and a distal end, and where the second anchoring member is longitudinally spaced proximally from the first anchoring member; and where both the first end and the second end of the support member are separately attached to the second anchoring member.

5. The frame of claim 4, where the support member extends diagonally across at an angle between about 15 degrees and about 60 degrees from the longitudinal axis and distally from the second anchoring member to the first anchoring member in the expanded configuration.

6. The frame of claim 1, where the first hinged attachment and the second hinged attachment are positioned on opposite sides of the longitudinal axis in the expanded configuration and are substantially aligned with the longitudinal axis in the compressed configuration.

7. The frame of claim 1, where the second hinged attachment connects the first end of the support member to the second anchoring member and a third hinged attachment connects the second end to the second anchoring member; the second hinged attachment being opposably positioned with respect to the third hinged attachment across the longitudinal axis.

8. The frame of claim 7, where the support member further comprises a first loop at the vertex, and the first hinged attachment is formed by interconnecting a portion of the first anchoring member with the first loop to form a hinged attachment between the vertex of the support member and the first anchoring member.

9. The frame of claim 7, where the support member further comprises a second loop at the first end and a third loop at the second end; the second hinged attachment being formed by interconnecting a first portion of the second anchoring member positioned within the second loop, and the third hinged attachment being formed by interconnecting a second portion of the second anchoring member positioned within the third loop.

10. The frame of claim 9, where the second loop and the third loop have a first inner diameter and the first portion of the second anchoring member and the second portion of the second anchoring member are loops having a thickness that is less than the first inner diameter of the second loop and the third loop, and the second hinged attachment and the third hinged attachment are formed as interconnecting loops.

11. The frame of claim 1, where each of the first anchoring member and the second anchoring member comprise an annular array of struts interconnected by a plurality of bends; and the first anchoring member and the second anchoring member are similarly shaped and oriented in mirror symmetry to each other.

12. The frame of claim 1, where the semielliptical curved support member defines an opening and the valve member is positioned within said opening.

13. The frame of claim 1 where the first anchoring member and the second anchoring member have different diameters in the expanded configuration.

14. The frame of claim 7, where the support member further comprises a first aperture at the vertex, and the first hinged attachment is formed by interconnecting a portion of the first anchoring member with the first aperture to form a hinged attachment between the vertex of the support member and the first anchoring member.

15. The frame of claim 7, where the support member further comprises a second aperture at the first end and a third aperture at the second end; the second hinged attachment being formed by interconnecting a first portion of the second anchoring member positioned within the second aperture, and the third hinged attachment being formed by interconnecting a second portion of the second anchoring member positioned within the third aperture.

16. The frame of claim 15, where the second aperture and the third aperture have a first inner diameter and the first portion of the second anchoring member and the second portion of the second anchoring member have a thickness that is less than the first inner diameter of the second aperture and the third aperture, and the second hinged attachment is formed by interconnecting the first portion of the second anchoring member positioned within the second aperture and the third hinged attachment is formed by interconnecting the second portion of the second anchoring member positioned within the third aperture.

* * * * *

UNITED STATES PATENT AND TRADEMARK OFFICE
CERTIFICATE OF CORRECTION

| | | |
|---|---|---|
| PATENT NO. | : 7,955,377 B2 | Page 1 of 1 |
| APPLICATION NO. | : 12/357646 | |
| DATED | : June 7, 2011 | |
| INVENTOR(S) | : Jeffry S. Melsheimer | |

It is certified that error appears in the above-identified patent and that said Letters Patent is hereby corrected as shown below:

Column 22, line 32 (Claim 3, line 7) reads --flow path and a dosed position--. It should read --flow path and a closed position--.

Signed and Sealed this
Twenty-third Day of August, 2011

David J. Kappos
*Director of the United States Patent and Trademark Office*